United States Patent [19]
Nichols et al.

[11] Patent Number: 5,853,884
[45] Date of Patent: Dec. 29, 1998

[54] METHOD FOR PRODUCING UNSUPPORTED FIBER BUNDLES FOR HME AND OTHER FILTRATION APPLICATIONS

[75] Inventors: Randall W. Nichols, Westlake; James C. Davis, Hudson, both of Ohio

[73] Assignee: Whatman, Inc., Mass.

[21] Appl. No.: 825,165

[22] Filed: Mar. 26, 1997

Related U.S. Application Data

[60] Provisional application No. 60/014,647 Apr. 1, 1996.

[51] Int. Cl.⁶ .............................. D02G 3/00; B29C 65/00; A62B 18/08
[52] U.S. Cl. .......................... 428/398; 428/375; 428/376; 428/364; 264/41; 264/558; 264/561; 264/563; 55/527; 55/528; 210/500.23; 210/506; 128/201.13; 128/204.13
[58] Field of Search ..................................... 428/398, 376; 264/41, 558, 561, 563; 55/527, 528; 210/500.23, 506; 128/201.13, 204.13

[56] References Cited

U.S. PATENT DOCUMENTS

| | | |
|---|---|---|
| 4,239,729 | 12/1980 | Hasegawa et al. . |
| 4,327,717 | 5/1982 | Oetjen et al. . |
| 4,749,619 | 6/1988 | Angleraud . |
| 4,900,626 | 2/1990 | Fabre . |
| 5,558,936 | 9/1996 | Chung et al. . |

FOREIGN PATENT DOCUMENTS

| | | |
|---|---|---|
| 299381 | 1/1989 | European Pat. Off. . |
| 343247 | 11/1989 | European Pat. Off. . |
| 378168 | 7/1990 | European Pat. Off. . |
| WO9736742 | 10/1997 | WIPO . |

*Primary Examiner*—A. A. Turner
*Assistant Examiner*—J. M. Gray
*Attorney, Agent, or Firm*—Fay, Sharpe, Beall, Fagan, Minnich & McKee

[57] ABSTRACT

A method for forming a hollow fiber bundle unit for insertion into an assisted breathing device comprising spinning a hollow fiber or hollow fibers, collecting multiple fibers into a bundle, filling the walls of the hollow fibers within the hollow fiber bundle with an humectant, coating the hollow fibers containing the humectant with a solution of an adhesive material, forming and drying the hollow fiber bundle coated with the solution, and preparing the hollow fiber bundle coated with the solution for insertion into the assisted breathing device.

15 Claims, 2 Drawing Sheets

METHOD FOR PRODUCING UNSUPPORTED FIBER BUNDLES FOR HME AND OTHER FILTRATION APPLICATIONS

This application claims priority from application Ser. No. 60/014,647 filed Apr. 1, 1996, now abandoned.

BACKGROUND OF THE INVENTION

The subject invention relates to a method for manufacturing hollow fiber bundles for use in assisted breathing apparatus, and to the hollow fiber bundles created by the inventive manufacturing process. More specifically, the invention relates to a method for coating the exterior of the hollow fibers to increase fiber stability and bundle strength, to increase active fiber area and also bundle size, and to reduce manufacturing costs and complexity.

In many medical applications, oxygen or air is administered to a patient on a long term basis, either through breathing tubes or an apparatus applied to the patient's mouth or nasal cavities, or more directly to the trachea of the patient by way of a tracheotomy. In such instances, however, there is oftentimes a problem with the drying out of the patient's nasal passages and lungs. This is a result of the patient's air supply having by-passed the patient's mouth and nasal cavities where natural breathing activity provides heat and moisture exchange mechanism for the inhaled oxygen.

In an effort to correct the foregoing problem, devices have been developed which pass the patient's breathing supply through a hydration device, for instance a bubbler bottle containing distilled water. Another device currently available for the use of assisted breathing devices is a product comprising treated corrugated paper. However, this device has limited application and life due to a non-uniform gas flow, a result of differing hole sizes in the corrugated paper, and due to surface area limitations resulting from the size restrictions on the device.

A suitable alternative to the corrugated paper filter is the use of a hollow fiber bundle, which affords uniform and easily controllable tube ID. The bundle may comprise any hollow fiber material suitable for reversible heat and moisture exchange. For example, U.S. Pat. No. 4,327,717 provides a humidity exchanger for a breathing apparatus comprising a module housing containing hollow fibers arranged longitudinally therein so as to allow expired air to traverse the outer surface of the fibers and inspired air to traverse the inner bores of the fibers. Further improvement to the '717 device has been developed whereby the fibers include, either within the fiber or within the pores thereof, the use of a humectant.

What has remained for the subject invention to provide is a means of foregoing large and bulky assisted breathing devices wherein the fiber bundles or the means of traversing inspired and expired gas or air through the device, in order to humidify the gas or air supply for the comfort of the user, is uniform.

It is an object of the subject invention, therefore, to provide a means of supplying a dimensionally stable hollow fiber unit, for use in an assisted breathing device, which offers uniformity and dimensional strength. In prior art breathing devices the dendritic form of the typical cellulosic paper products may generate dust from cutting or friability during handling resulting in a serious problem for the user. The synthetic polymeric nature of the hollow fibers and the binder affect of the coating polymer used in the current design eliminate these problems.

It is another object of the subject invention to provide a method of manufacturing hollow fiber units for use in assisted breathing apparatus or devices wherein the fibers, and the fiber bundles, are coated so as to increase dimensional stability of the fibers and the bundles.

It is yet another object of the invention to provide hollow fiber units which are small in size as compared to existing units, and which nonetheless provide increased hollow fiber surface area, and which exhibit dimensional stability, thus enhancing use and reducing manufacturing costs.

SUMMARY OF THE INVENTION

The invention relates to a method for forming a hollow fiber bundle unit for insertion into an assisted breathing device. The method comprises spinning a hollow fiber or fibers, collecting multiple fibers into a bundle, filling the walls of the hollow fibers within the hollow fiber bundle with an humectant, coating the hollow fibers containing the humectant with a solution of an adhesive material, forming and drying the hollow fiber bundle coated with the solution, and preparing the hollow fiber bundle coated with the solution for insertion into the assisted breathing device.

DETAILED DESCRIPTION OF THE INVENTION

Figure 1:
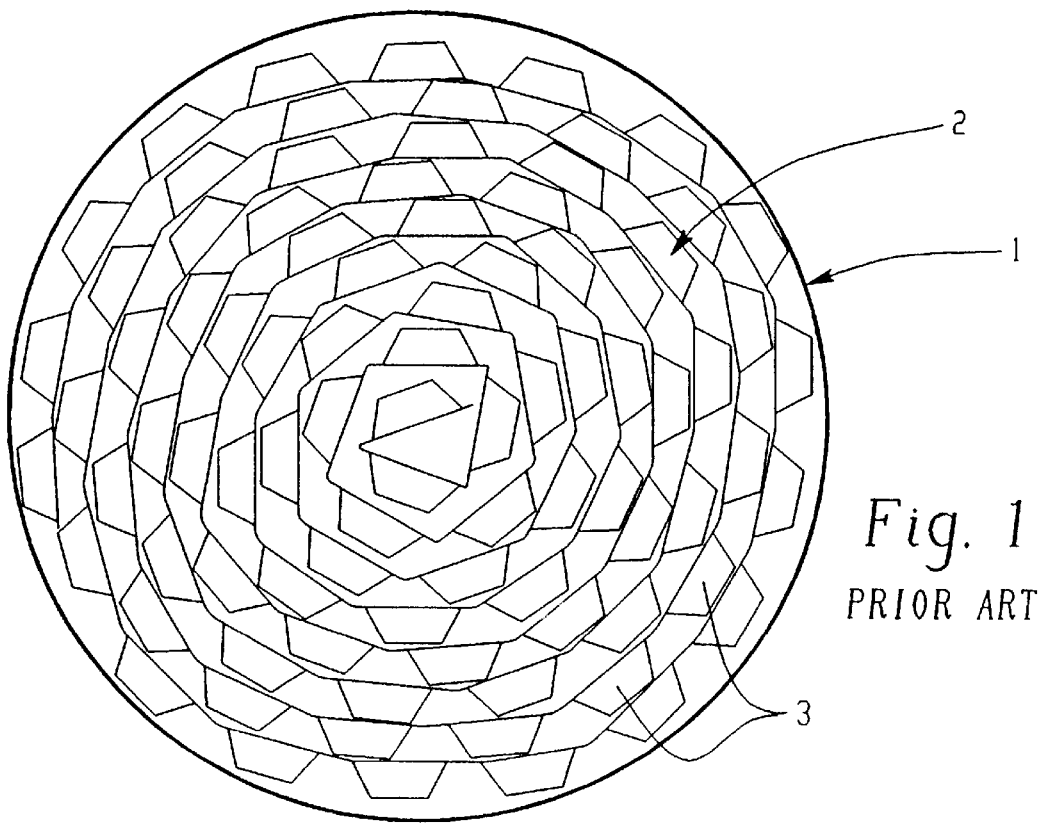
FIG. 1 represents a cross-sectional view of a Prior Art assisted breathing device, comprising wrapped corrugated paper.

The subject invention relates to a method of manufacturing hollow fiber bundles of the type intended for use in assisted breathing apparatus. Specifically, the invention relates to a method for manufacturing hollow fiber bundle units for use in assisted breathing devices or apparatus comprising: spinning hollow fibers; filling the hollow fiber walls of the fibers with a solution of a highly water absorptive material, i.e. an humectant; and then binding the bundle with a coating on the fiber exteriors of a polymeric adhesive. The filler assists in increasing the heat and moisture exchange function or capability of the bundle. The binder or coating is intended to serve several functions. For instance, the binder or coating will eliminate problems due to fiber crushing which may occur when using wrapping material to stabilize and contain the bundle. Also, the need for such wrapping is eliminated, thereby reducing cost and affording an increase in active fiber bundle size. The inventive coating further affords the use of fibers having a parallel orientation, thereby increasing the amount of fiber which can be used in a bundle of a given size. Finally, larger, thinner fiber wafers may be constructed because the coating provides greater stability in cutting and handling the bundles.

The design of the housing of the assisted breathing unit is not intended to be a part of this invention as such housing units are well known in the art to which this invention pertains. Therefore, while no detail of the housing and exterior connections for the housing into which the subject hollow fiber units are intended to be inserted will be set forth herein, it is assumed that the skilled artisan will readily appreciate the manner in which the units will be usable in such existing devices.

The hollow fibers themselves may be prepared according to known methods for spinning or drawing hollow fibers. Suitable hollow fiber materials include cellulosics, polyvinylidenedifluoride (PVDF), polysulfone, polyethersulfone, polyimides, polyamides, polyesters, polyphenyleneoxide, polyphenylenesulfide, polycarbonate, and the like. Preferred herein are polysulfone and polyethersulfone.

The hollow fibers of the subject invention are intended to be filled with an humectant material which will aid in the exchange of moisture to and from the inspired and expired gas/air supply. Suitable humectants include, but are not limited to, glycerol, other polyols, calcium chloride, and other known hygroscopic salts and hygroscopic compounds.

The hollow fibers, once loaded with an appropriate humectant, are coated with a material which serves in the manner of a binder to eliminate many of the problems of prior art devices concerning dimensional stability. Once coated, the fibers will more successfully resist cruching or fraying, either during preparation or during use. The fibers are coated with the coating material by drawing the bundle through a bath or by submerging the bundle in a bath. Alternatively, the coating solution may be sprayed or poured onto the fiber before or after forming the bundle.

Suitable binder materials include solutions of adhesive material. For example, the solution may comprise a highly water absorptive polymer, such as polyvinyl alcohol, polyvinyl pyrrolidone, and other water soluble polymers. The polymer may be cross-linked for additional stability after coating. The coating allows the bundle to be formed into a cylinder of precise dimensions, by pulling the bundle through an appropriately sized die. By drying the bundle in that configuration, a rod or cable of fiber bundle is formed which can then be sliced into wafers for insertion into an assisted breathing device.

The following example provides a method by which hollow fiber units of the type intended herein can be prepared. The example is intended only as a means of better educating the skilled artisan to the manner of performing the invention, and is not intended to limitative thereof in any way, as the skilled artisan will be able to anticipate slight alterations to the following, which are nonetheless intended as part of this invention.

EXAMPLE 1

A polysulfone hollow fiber of Amoco Udel P1835 (30.4%), GAF K-30 Polyvinylpyrrolidone (10.1%) and BASF N-methylpyrrolidone (59.5%) was phase inversion spun into a water quench bath providing wet fibers having an 900 micron outer diameter and a 700 micron inner diameter. The wet fibers were rinsed in water to remove residual solvent and then soaked in 10 to 25% calcium chloride to impact moisture exchange capacity. After drying the fiber, the bundle was wrapped onto a second core with the exact number of fibers required. A tape was used to control the ends of the fibers during cutting to achieve a fiber mat. Prior to cutting, the fibers were coated with a 4% aqueous solution of polyvinyl alcohol (PVA) and subsequently spun at high speed about the axis of the core to remove excess polymer solution. The bundle was cut, rolled up into a cylindrical configuration, the tape cut off of one end of the bundle to allow free fiber movement, and the bundle was pulled through a die to form a cylinder of the desired diameter. The bundle was heated as it was pulled through the die to dry the outer coating of PVA. Alternatively, the bundle could be constrained in a tube of appropriate inner diameter and oven dried with a flow of warm air blowing through the fibers. Subsequent to drying into a rigid, cylindrical form, the rod was sliced into wafers of the thickness for the device in which it is intended to be encapsulated.

Figure 2:
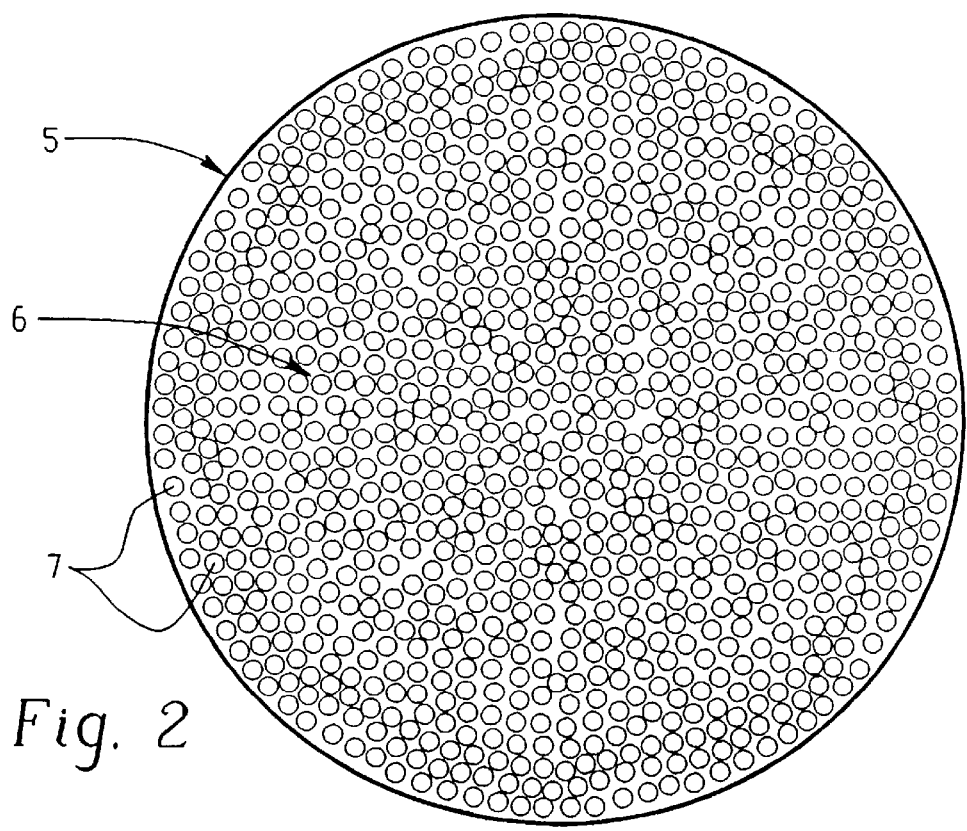
FIG. 2 represents a cross-sectional view of the hollow fiber bundle constructed in accord with the subject inventive method.

FIG. 1 represents a cross-sectional view of a prior art device, comprising wrapped corrugated paper. In this FIG. 1, the prior art device shown comprises a housing 1, which contains a wound corrugated paper bundle 2. The openings in the corrugated paper 3 are also shown. The gas or air passed through the device travels longitudinally through the tunnels formed by the openings in the corrugated paper. In the current invention design, as shown in FIG. 2, the housing 5 contains a hollow fiber bundle constructed according to the method herein. The hollow fiber bundle 6 comprises fibers which extend longitudinally in a tightly packed arrangement within the housing 5. This arrangement, shown in a cross-sectional view, provides for a more uniform, dense packing of fibers, the open ends 7 of which are shown in FIG. 2. Gas or air flow, as in the prior art design shown in FIG. 1, is longitudinal through the bundle in the hollow fiber unit, as indicated by the arrow on the FIGURE. It is easily seen that the invention hollow fiber bundle, depicted in cross-section in FIG. 2, provides increased surface area for the exchange of moisture to and from inspired and expired gas or air over the prior art design. The coating or binding which is the subject hereof would be found on the exterior surfaces of the fibers comprising the hollow fiber bundle shown in FIG. 2, as well as over the exterior surface of the bundle as a whole. It is this coating or binding material which provides the rigidity necessary to be able to cut a hollow fiber bundle transversely, or cross-sectionally, to create discs suitable for insertion into a breathing device without crushing the fibers, i.e., the coated fibers maintain their dimension stability which provides for ease in handling and use, without threat of fiber crushing.

The following data demonstrates the performance capability of a hollow fiber bundle prepared in accord with the foregoing inventive process as compared to the performance of a prior art assisted breathing device.

Figure 3:
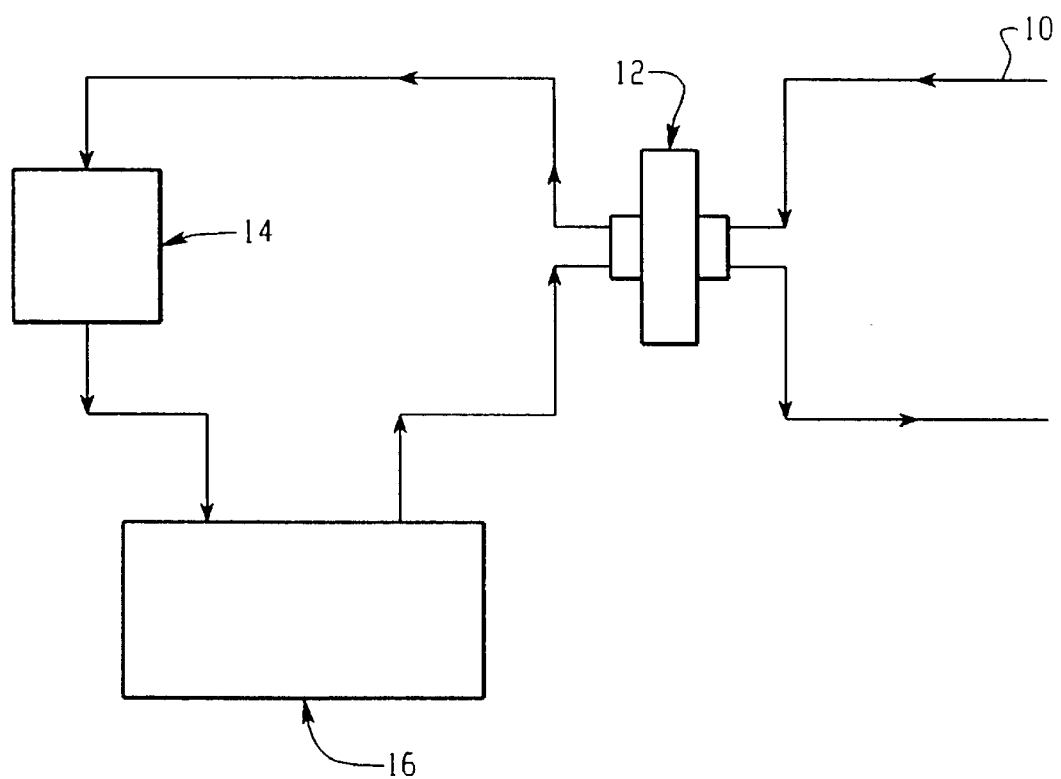
FIG. 3 represents a schematic for the test system used to compare the inventive device which is the subject hereof to existing devices.

More specifically, hollow fiber bundles prepared in accordance with Example 1 and a prior art conventional cellulosic material (corrugated paper) were tested for heat and moisture exchange (HME) and pressure drop characteristics. Sample 1 was made of 460 μm outer diameter hollow fibers fabricated into a bundle 0.92 inches in diameter and 0.4 inches long, impregnated with glycerol humectant. Sample 2 was made of 550 μm outer diameter fibers made into a bundle similar to the bundle of sample 1 with glycerol humectant. Sample 3 was a bundle similar in configuration and composition to that of Samples 1 and 2 having 700 μm outer diameter fibers and with calcium chloride humectant. Sample 4 was a prior art device available commercially as a Portex Thermovent 600 from Sims (Smiths Industries Medical Systems). Each of the Sample 1–3 bundles was coated with PVA. The test involved insertion of the sample into a conventional breathing apparatus housing, the Portex Thermovent 600, which holds the filter during normal breathing action. As shown in FIG. 3, dry air is passed through the HME (12) into an artificial lung (14). The air drawn from the lung (14) passes through a water bath at 34° C., which warms and humidifies the air, and then travels back through the HME (12) in the opposite direction. The amount of moisture absorbed is determined gravimetrically after a specified period of time.

Table I comprises the result of a brief assessment of humidifying capacity for Samples 1–4. The results demonstrate that the hollow fiber samples according to the subject invention display a comparable humidifying performance as compared to the cellulose design.

TABLE I

Humidifying Capacity*

| HME Configuration | Moisture output (mg/1) |
|---|---|
| 460 µm + Glycerol | 23.4 |
| 55 µm + Glycerol | 19.7 |
| 700 µm + Glycerol | 22.2 |
| Conventional Cellulose | 22.3 |

*0.5 liter tidal volume
20 breaths per minute
Inspiratory: Expiratory rate ratio = 1.8:1.0

Table II shows the results for Samples 1 and 4 when tested as above, but for extended periods of time. The Sample according to the invention is again shown to perform comparably to the conventional design.

TABLE II

Humidifying Capacity at Extended Time Period

| HME Configuration | Moisture Output | |
|---|---|---|
| | 1–3 Hours | 1–24 Hours |
| 460 µm Glycerol | 22.1 | 22.7 |
| Conventional Cellulose | 22.8 | 22.8 |

Table III demonstrates the results of testing to establish the pressure drop across the test unit for Samples 1 and 4, both before and after 24 hour use and at varying flow rates. Sample 1 according to the invention demonstrates a slightly higher pressure drop, but nonetheless operates within standard parameters for acceptable performance of the test unit.

TABLE III

Pressure Drop

| HME Configuration | Flow (1/min) | Pressure Drop (cm H$_2$O) | | Typical Specification |
|---|---|---|---|---|
| | | Initial | Final | |
| 460 µm + Glycerol | 30 | 1.28 | 1.32 | 0.5–1.5 |
| | 60 | 3.17 | 3.24 | 2.4–3.4 |
| | 90 | 5.73 | 5.89 | 3.2–6.2 |
| Conventional Cellulose | 30 | 0.79 | 0.85 | 0.5–1.5 |
| | 60 | 2.25 | 2.41 | 2.4–3.4 |
| | 90 | 4.46 | 4.75 | 5.2–6.2 |

The foregoing demonstrates the suitability of hollow fiber bundles prepared in accord with the method set forth herein for use in the intended manner. The coating or binder which is used on the hollow fiber bundles enhances the dimensional stability of the hollow fiber units, and decreases production costs, thus making hollow fiber units prepared in accord with this invention a very viable and attractive alternative to existing units. The full breadth and scope of the invention is to be determined by the claims appended hereto, and not limited to any specific example provided herein for the understanding of the reader.

We claim:

1. A method for forming a hollow fiber bundle unit for insertion into an assisted breathing device comprising:
    spinning at least one hollow fiber;
    collecting the hollow fiber into a bundle;
    filling the walls of the hollow fibers within the hollow fiber bundle with an humectant;
    coating the hollow fibers containing the humectant with a solution of an adhesive material;
    forming and drying the hollow fiber bundle coated with the solution; and
    preparing the hollow fiber bundle coated with the solution for insertion into the assisted breathing device.

2. The method of claim 1 wherein the hollow fibers of the hollow fiber bundle contain a humectant selected from the group consisting of glycerol, polyol, and calcium chloride.

3. The method of claim 1 wherein the coating solution comprises water and a polymer selected from the group consisting of polyvinyl alcohol and polyvinyl pyrrolidone, or a combination thereof.

4. The method of claim 1 wherein the hollow fibers coated with the solution are formed into a bundle of a suitable dimension by pulling the fiber bundle through a die of a size and shape in keeping with the dimensions of the assisted breathing device.

5. The method of claim 4 wherein the bundle, pulled though the die, is maintained in the configuration achieved by pulling the bundle through the die and dried in that configuration.

6. The method of claim 5 further including the step of cutting the bundle into discs for insertion into the assisted breathing device.

7. A coated hollow fiber bundle unit for insertion into an assisted breathing device comprising a multiplicity of hollow fibers collected into a hollow fiber bundle, the walls of the hollow fibers being filled with an humectant composition and the exterior surfaces of the hollow fibers and of the hollow fiber bundle being coated with a coating solution comprising an adhesive material.

8. The coated hollow fiber bundle unit of claim 7 wherein the humectant composition is selected from the group consisting of glycerol, polyol, and calcium chloride.

9. The coated hollow fiber bundle unit of claim 7 wherein the coating solution is an adhesive solution comprising a water soluble polymer selected from the group consisting of polyvinyl alcohol and polyvinyl pyrrolidone.

10. A method for forming a hollow fiber bundle unit for insertion into an assisted breathing device comprising:
    spinning a hollow fiber bundle;
    filling the hollow fibers within the hollow fiber bundle with an humectant;
    coating the hollow fibers filled with the humectant and forming the hollow fiber bundle with a solution comprising a water soluble, water absorptive polymer dissolved in water;
    forming the filled hollow fiber bundle into a bundle of a suitable dimension by pulling the fiber bundle through a die of a size and shape in keeping with the dimensions of the assisted breathing device;
    maintaining the bundle in the configuration achieved by pulling the bundle through the die and drying the filled hollow fiber bundle in that configuration;
    cutting the bundle into discs for insertion into the assisted breathing device; and
    fitting the configured, filled hollow fiber bundle coated with the solution for insertion into the assisted breathing device.

11. The method of claim 10 wherein the hollow fibers of the hollow fiber bundle are filled with a humectant selected from the group consisting of glycerol and calcium chloride.

12. The method of claim 10 wherein the coating solution comprises water and a polymer selected from the group consisting of polyvinyl alcohol and polyvinyl pyrrolidone, or a combination thereof.

13. A coated hollow fiber bundle unit for insertion into an assisted breathing device comprising a multiplicity of hollow fibers collected into a hollow fiber bundle and drawn through a die to a certain configuration of a size and shape in keeping with the dimensions of the assisted breathing device and dried in the drawn configuration, the walls of the hollow fibers being filled with an humectant composition and the exterior surfaces of the hollow fibers and of the hollow fiber bundle being coated with a coating solution comprising an adhesive material.

14. The coated hollow fiber bundle unit of claim 13 wherein the humectant composition is selected from the group consisting of glycerol and calcium chloride.

15. The coated hollow fiber bundle unit of claim 13 wherein the coating solution is an adhesive solution comprising a water soluble polymer selected from the group consisting of polyvinyl alcohol and polyvinyl pyrrolidone.

* * * * *